US009655568B2

(12) United States Patent  
Ritschl

(10) Patent No.: US 9,655,568 B2  
(45) Date of Patent: May 23, 2017

(54) METHOD FOR RECORDING A COMPLETE PROJECTION DATA SET IN THE CENTRAL LAYER FOR CT RECONSTRUCTION USING A C-ARM X-RAY APPARATUS WITH A LIMITED ROTATION RANGE

(71) Applicant: Ziehm Imaging GmbH, Nürnberg (DE)

(72) Inventor: Ludwig Ritschl, Erlangen (DE)

(73) Assignee: Ziehm Imaging GmbH, Nürnberg (DE)

( * ) Notice: Subject to any disclaimer, the term of this patent is extended or adjusted under 35 U.S.C. 154(b) by 295 days.

(21) Appl. No.: 14/458,172

(22) Filed: Aug. 12, 2014

(65) Prior Publication Data

US 2015/0049856 A1 Feb. 19, 2015

(30) Foreign Application Priority Data

Aug. 14, 2013 (DE) .................. 10 2013 013 552

(51) Int. Cl.

| H05G 1/02 | (2006.01) |
| A61B 6/03 | (2006.01) |
| A61B 6/00 | (2006.01) |

(52) U.S. Cl.  
CPC ............ *A61B 6/035* (2013.01); *A61B 6/4028* (2013.01); *A61B 6/4078* (2013.01);  
(Continued)

(58) Field of Classification Search  
CPC ..... A61B 6/035; A61B 6/4028; A61B 6/4405; A61B 6/4441  
(Continued)

(56) References Cited

U.S. PATENT DOCUMENTS

| 4,138,721 A | 2/1979 | Boyd |
| 5,032,990 A | 7/1991 | Eberhard et al. |

(Continued)

FOREIGN PATENT DOCUMENTS

| DE | 26 04 020 C3 | 12/1980 |
| DE | 40 162 45 C2 | 7/1994 |

(Continued)

OTHER PUBLICATIONS

Dennerlein, et al. "Cone-beam reconstruction from a variable-radius planar source trajectory," 2009 IEEE Nuclear Science Symposium Conference Record, 2009, pp. 2496-2499.  
Noo, et al. "Image reconstruction from fan-beam projections on less than a short scan," Physics in Medicine and Biology, No. 47, Jul. 2002, pp. 2525-2546.

*Primary Examiner* — Courtney Thomas  
(74) *Attorney, Agent, or Firm* — Knobbe, Martens, Olson & Bear LLP

(57) ABSTRACT

A method for recording a scan from a series of 2D X-ray projections using a C-arm X-ray apparatus allows an analytical volume reconstruction of a disk-shaped region of interest. The C-arm X-ray apparatus has a coherent, flat focus trajectory comprising three sections on which the focus of the X-ray source is moved with recording of X-ray projection views. The X-ray source emits a cone beam in the direction of an imaging X-ray detector, such as in particular a flat panel detector FPD. In some implementations, the cone beam is configured as a fan beam with a fan angle in the plane of the focus trajectory, which contains the ROI with the virtual scan center in its center, wherein the central ray of the fan beam is located on the bisector of the fan angle, and stands vertically on the ray inlet window. Before the beginning of the scan, the C-arm is positioned in the orbital movement axis in a first extreme position in which the holder engages at one end of the C-arm with the X-ray source, and the adjustable holder of the C-arm is positioned (Continued)

in such a manner that the ROI is located outside of the circle segment formed by the C-arm and the central ray, and a first limiting beam of the fan beam, which starts from the focus point and which is located on the side of the central ray facing away from the C-arm, is tangential to the ROI. During the recording of the scan, the plane of the C-arm remains fixed in space.

6 Claims, 4 Drawing Sheets

(52) U.S. Cl.
CPC .......... *A61B 6/4405* (2013.01); *A61B 6/4441* (2013.01); *A61B 6/5205* (2013.01); *H05G 1/02* (2013.01)

(58) Field of Classification Search
USPC .................................................. 378/193–198
See application file for complete search history.

(56) References Cited

U.S. PATENT DOCUMENTS

| | | | |
|---|---|---|---|
| 5,155,756 | A * | 10/1992 | Pare ..................... A61B 6/0457 378/193 |
| 8,284,892 | B2 | 10/2012 | Pack et al. |

FOREIGN PATENT DOCUMENTS

| | | |
|---|---|---|
| DE | 102 24 011 A1 | 12/2003 |
| DE | 101 53 787 B4 | 4/2005 |
| DE | 20 2005 021 106 U1 | 3/2007 |
| DE | 10 2006 037 564 B3 | 3/2008 |
| DE | 10 2009 031 165 A1 | 1/2011 |
| DE | 10 2009 038 787 A1 | 3/2011 |
| DE | 10 2011 086 754 A1 | 5/2013 |

* cited by examiner

METHOD FOR RECORDING A COMPLETE PROJECTION DATA SET IN THE CENTRAL LAYER FOR CT RECONSTRUCTION USING A C-ARM X-RAY APPARATUS WITH A LIMITED ROTATION RANGE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to C-arm X-ray imaging systems, and in particular, relates to methods for recording scans in a region of interest for CT reconstruction using C-arm X-ray imaging systems.

Description of the Related Art

In interventional X-ray diagnostics, mobile C-arm X-ray apparatuses are being used to an increasing extent. Such a C-arm X-ray apparatus is movable on the floor and it carries, on a chassis, a multiply adjustable holder in which a circular arc-shaped C-arm can be adjusted along its periphery in an orbital movement, wherein the C-arm carries an X-ray source at one end and an imaging X-ray detector at the other end, preferably a flat panel detector (FPD). It is preferable for all the adjustment axes to be provided with electrically controllable drives, so that, by means of a movement control, the X-ray recording unit consisting of the X-ray source and the X-ray detector can be positioned in the room and/or moved along a focus trajectory. After a positioning of the X-ray recording unit or also during the movement on a focus trajectory, X-ray projection views are prepared. If the X-ray detector has a round inlet window, such as, for example, in the case of an X-ray image amplifier or in the case of a round FPD, then the radiation field between the focal spot of the X-ray tubes is conical; in the case of the use of a rectangular FPD, the radiation field is pyramidal. In both cases, the term cone beam geometry ("cone beam," abbreviated "CB") is used in the literature. The radiation field is collimated in such a manner by a primary radiation diaphragm that all the rays of the radiation field fall onto the inlet window of the X-ray detector. If an examination object is introduced into the radiation field, then an X-ray projection of the spatial region of the examination object located within the radiation field can be recorded. In order to delimit the radiation field to a region of interest (Region of Interest, ROI), a diaphragm system that can preferably be adjusted by means of a motor is arranged between the focal spot and the examination object. All the image recording processes are controlled by an image recording control that is synchronized with the movement control. The recorded X-ray projection views are processed together with the data from the movement control and the image recording control in an image processing computer.

In the case of interventional X-ray diagnostics, the region around the patient bench is occupied by a number of apparatuses and, in addition, a working area must be provided for the persons performing the intervention or assisting during the intervention. A mobile C-arm X-ray apparatus used for the interventional diagnostics is moved toward the examination object, preferably approximately perpendicularly to the longitudinal axis of the patient bench, so that the C-arm plane contains the ROI approximately. In this work position, the wheels of the chassis are preferably blocked and the X-ray recording unit of the C-arm X-ray apparatus is moved by means of several adjustment axes, preferably controlled by means of a motor, into the desired position and alignment. If scans for recording an image series of projection images are produced during the intervention, then it is desirable that the movement of the X-ray recording unit and of the central ray remains in an initially set plane. Each movement component perpendicular to the original C-arm plane would increase the space requirement of the C-arm X-ray apparatus in the direction of the longitudinal axis of the patient bench and generate an increased risk of collision with other apparatuses and/or reduce the working space for the persons participating in the intervention. For handling the C-arm X-ray apparatus, it is particularly advantageous if the C-arm plane is vertical in the room. Then, only a small corridor needs to be kept clear as movement space for the movement of the X-ray recording unit during a scan. When the mobile C-arm X-ray apparatus is not in use for a brief time, it can be moved on wheels attached to a chassis on the floor from the patient bench approximately perpendicularly to the longitudinal axis of the patient bench from the latter into a parked position, and from said parked position it can be quickly moved back into the work position.

For the reconstruction of the X-ray volume of an ROI, the image data of a series of 2D X-ray projections of the ROI are needed, which have been recorded with different X-ray projection geometries. Here, the X-ray source and the imaging X-ray detector, for example, a flat panel detector FPD, move around the ROI, wherein, during the movement, X-ray projection views of the examination object are prepared.

With mobile C-arm X-ray apparatuses, it is preferable to record short scans if the rotation angle range is smaller than 360°. If the C-arm X-ray apparatus has an isocentric C-arm, in the case of which the central ray extends through the circle center of the C-arm, it is possible, by rotating the C-arm around its center, to record a flat rotation scan whose rotation angle range depends on the arc length and the radius of the C-arm.

If the C-arm X-ray apparatus has a non-isocentric C-arm, in which the circle center of the C-arm is located within the segment of a circle formed by the central ray and the C-arm profile, then, with such a non-isocentric C-arm X-ray apparatus, a rotation scan can be recorded as with an isocentric C-arm, if the X-ray recording unit is moved around a virtual isocenter in such a manner that the holder of the C-arm is adjusted in the C-arm plane for each scanning position in such a manner that the central ray extends through the virtual scan center. Here, the adjustment of the C-arm holder can occur in such a manner that the distance from the inlet window of the X-ray detector to the virtual scan center is the same for every projection geometry. However, it is also possible to record scans with variable distance between the inlet window of the X-ray detector and the virtual scan center with equal distance between the X-ray tube assembly and the X-ray receiver.

In order to be able to determine the 2D model of the X-ray absorption of the voxels of a disk-shaped ROI having the thickness of one voxel, from a set of X-ray projections using analytical computation methods, a complete projection data set is required. In this projection data set, for each voxel of the ROI, the integrals of the X-ray absorption values are available for all the projection lines in an angle range from 0° to 180°.

A complete projection data set is obtained for a disk-shaped ROI in the C-arm plane if the ROI is acquired completely by a fan beam and if the X-ray recording unit associated with the fan beam is rotated around the center of the ROI with a rotation angle range of 180° plus fan angle.

Complete projection data sets for the reconstruction of a 3D ROI can only be recorded with non-flat trajectories of the focus of the X-ray source. Thus, for example, short spiral scans, circle+line scans or circle-arc scans can be recorded with a C-arm X-ray apparatus, if the adjustment of the C-arm holder allows a movement perpendicular to the C-arm plane.

A projection data set that is complete for a disk-shaped ROI in the central layer and that was recorded with a cone beam geometry can also be used outside of the central layer as an approximation by applying a Feldkamp algorithm for the reconstruction.

If a disk-shaped X-ray volume is reconstructed from an incomplete projection data set, then artifacts occur in the reconstructed X-ray volume, which strongly interfere with a diagnosis of the conditions in the ROI. Therefore, it is desirable to minimize the artifacts in the ROI by recording a complete projection data set.

C-arm X-ray apparatuses with a scanning angle range of the central ray of 180° plus fan angle are known and used predominantly in stationary X-ray diagnostic devices. Typical values of the fan angle in common C-arm systems are values between 10° and 20° In order to obtain a complete set of projection data for the 3D reconstruction, a rotation angle range of the orbital movement of 200° would be needed in the case of a fan angle of 20°. In C-arm apparatuses in which the C-arm is mounted in a holder so it can be moved along its periphery, the C-arm would have to have an arc length that is increased by the angle range of the holder, that is, 200° plus angle range of the holder. In comparison to a semicircular C-arm with a with a 180° arc length and identical radius of the C-arm, a C-arm with an arc length of 200° plus angle range of the holder has a smaller opening width between the ends of the C-arm. In order to increase the opening width in the case of a given arc length, the radius of the C-arm has to be increased, which, for the purpose of achieving a sufficient stability and torsional stiffness, results in an increase of the weight of the C-arm, and a more stable and heavier construction of the C-arm mobile tripod in order to be able to reliably compensate for the increased tilting torques of the enlarged and heavier C-arm. A C-arm X-ray apparatus with an increased radius is bulkier and heavier and consequently more difficult to handle and maneuver than a compact, mobile C-arm X-ray apparatus with a C-arm length of 180° and a smaller radius with the same opening width. In addition, the advantage of the good mobility of a small C-arm X-ray apparatus no longer exists with larger and heavier C-arm X-ray apparatuses.

DE202005021106U1 relates to a C-arm X-ray apparatus for the automatic generation of projection views for a volume reconstruction, by means of which can be set a stored sequence of adjustment positions of the horizontal, vertical and orbital adjustment axes, which can be adjusted in succession by means of an electric motor, wherein, for each setting, an X-ray projection view with a corresponding projection geometry is recorded.

DE10153787B4 relates to a mobile X-ray diagnostic device with a non-isocentric C-arm that can be moved along its periphery, with a C-arm holder that can be adjusted by means of a motor in terms of least two axes, and with a movement control, which performs the setting of the axes controlled by means of a motor as a function of the position of the C-arm in the orbital axis in such a manner that, with the X-ray recording system, X-ray projection views can be recorded with a predetermined projection geometry. In particular, it is possible to reproduce an isocentric C-arm with a virtual isocenter.

U.S. Pat. No. 4,138,721A relates to a method for generating a limited 3D data set with a focus trajectory for a fan beam, in which the X-ray focus is moved so that the fan beam is moved transversely to the central ray over the ROI and, at the end points of the focus trajectory, the fan beam is located entirely outside of the ROI. The focus trajectory can consist of a line or of a circular arc, the radius of which is considerably smaller than the distance between the X-ray detector and the center of the ROI. Here, the ROI is moved into the radiation field and again out of the radiation field during the recording of X-ray projections.

DE102009031165A1 relates to a method for recording X-ray images of an ROI from several viewing angles for a 3D reconstruction using an X-ray image recording system, in which the X-ray source and the X-ray detector can be positioned separately from one another and aligned relative to one another, wherein the focus of the X-ray source, with recording of X-ray projections, is moved along a focus trajectory, which consists of a combination of straight line segments and/or arc segments, in such a way that the ROI is projected completely onto the X-ray detector at the time of each recording. The line and/or arc segments can be connected to one another and can be located in a plane.

DE10224011A1 discloses a computer-assisted reconstruction method for a three-dimensional object, in which the projection data were generated from an incomplete scan having a scanning range of less than 180°. For the reconstruction, assumptions are made regarding the X-ray transparency of the examination object.

DE102009038787A1 discloses a method for recording a 3D data set of an examination object in order to prevent cutting-off effects, wherein a first scan with a scan angle of 180° plus half a fan angle is recorded, and in the case of a second scan with the same scanning range, the X-ray detector is moved in the scanning direction.

DE4016245C2 relates to a method for recording a complete projection data set using a translation-rotation scanner for an object that exceeds the size of the beam fan.

DE102006037564B3 relates to a method for recording a 3D projection data set, in which, in order to prevent truncation effects, a robot-guided C-arm is tracked synchronously with respect to the rotation in the C-plane in such a manner that the region of interest is located, at least at the time of each rotation angle at which an image recording occurs, within the ray cone of an X-ray bundle of the image recording system.

DE2604020C3 relates to a rotatory scanning of an object with a fan beam and a scanning angle range of 180° plus a fan angle for recording a complete 3D projection data set, in which a diaphragm that can be adjusted depending on the scanning angle position, at the beginning of the scan, first removes a first marginal area of the fan beam and at the end of the scan the second marginal area of the fan beam, which results in a reduction of the patient dose.

DE102011086754A1 relates to a C-arm X-ray apparatus and to a method for the rotatory scanning of an object, in which the rotation of the C-arm is superposed by a shifting movement between the object and the C-arm. In the case of a complete scan with a scanning angle range of 180° plus fan angle, a larger volume can be reconstructed than in the case of a purely rotatory scanning.

U.S. Pat. No. 5,032,990A and the article by K. C. Tam, "Reducing the Fan-Beam Scanning Angular Range," Phys. Med. Biol., Volume 33 (1988), pp. 955-967, disclose that a mathematically error-free 3D reconstruction can be achieved with 2D projection data that were recorded in the case of a half scan with a flat circular trajectory with a central ray-related rotation angle range 180° plus fan angle.

U.S. Pat. No. 8,284,892B2 relates to a method and to a device for volume reconstruction from projection data that were recorded with a short scan. Redundant projection data are taken into consideration by weighting reconstructed partial volumes before the addition to a total volume.

From the article F. Dennerlein, H. Kunze, J. Boese "Cone-beam reconstruction from a variable-radius planar source trajectory" in 2009 IEEE Nuclear Science Symposium Conference Record (2009), pp. 2496-2499, a reconstruction method of the Feldkamp type is known, in which projection data from flat focus and detector trajectories of a short scan with an angle range of 180° plus fan angle are used. The short scan trajectories can be open rectangles or open trajectories having different radii. It is provided to allow the focus and detector trajectories to oscillate around a rectangular trajectory.

From the article F. Noo, M. Defrise, R. Clackdoyle, H. Kudo "Image reconstruction from fan-beam projections on less than a short scan," Phys. Med. Biol. 47 (2002) 2525-2546, published in July 2002, a super short scan method for recording a projection data set and for reconstructing a decentrally arranged ROI is known, wherein the scan angle around the rotation center can be less than 180° plus fan angle.

The methods for recording a scan for generating a projection data set with a C-arm X-ray apparatus with cone beam geometry that are known in the prior art, and wherein the apparatus in the plane of the C-arm has a fan beam geometry with a fan angle and the C-arm of which during the scan is moved in a space-fixed plane, have the disadvantage that a complete set of X-ray projections for the analytical reconstruction of a disk-shaped X-ray volume located in the plane of the C-arm requires an orbital angle adjustment range of at least 180°.

The aim of the invention is to provide a method for recording a scan for generating an X-ray projection view with a C-arm X-ray apparatus, wherein the C-arm X-ray apparatus has a cone beam geometry and in the plane of the C-arm fan beam geometry with a fan angle and an orbital angle adjustment range, and the C-arm of which, during the scan, is moved in a space-fixed plane, so that with the X-ray projection views, a complete set of X-ray projections is produced, for the analytical reconstruction of a disk-shaped X-ray volume of the central layer, which is located in the plane of the C-arm, with an orbital angle adjustment range of less than 180°.

SUMMARY OF THE INVENTION

The aim of the invention is achieved by a method according to Claim 1.

The method according to embodiments of the invention for recording a scan from a series of 2D X-ray projections with a C-arm X-ray apparatus, which allow an analytical volume reconstruction of a disk-shaped ROI of the central layer, has a coherent, flat focus trajectory comprising three sections, on which the focus of the X-ray source is moved with recording of X-ray projection views, wherein the X-ray source emits a cone beam in the direction of an imaging X-ray detector, such as in particular a flat panel detector FPD. In one embodiment, the cone beam is configured as a fan beam with a fan angle in the plane of the focus trajectory, which contains the ROI with the virtual scan center in its center, wherein the central ray of the fan beam is located on the bisector of the fan angle, and stands vertically on the ray inlet window. In the context of certain embodiments of the invention, it is provided that, for a disk-shaped ROI in the central layer, the complete projection data set, which was recorded with a cone beam geometry, is also used outside of the central layer as an approximation by applying a Feldkamp algorithm for the reconstruction. Before the beginning of the scan, the C-arm plane is set up in the room, and the C-arm is positioned in the orbital movement axis in a first extreme position in which the holder engages at one end of the C-arm with the X-ray source, and the adjustable holder of the C-arm is positioned in such a manner that the ROI is located outside of the circle segment formed by the C-arm and the central ray, and a first limiting beam of the fan beam, which starts from the focus point and which is located on the side of the central ray facing away from the C-arm, is tangential to the ROI. During the recording of the scan, the plane of the C-arm remains fixed in space.

In the first of the three sections of the focuse trajectory, the C-arm remains positioned in the first extreme position of the orbital movement axis and the holder of the C-arm is moved parallel in the plane of the C-arm in a collision-free manner until the central ray extends through the virtual scan center and the ROI is located entirely within the fan beam.

In the second focus trajectory adjoining the first section, the C-arm is moved along the orbital movement axis from the first extreme position into the second extreme position which is turned 180° minus fan angle around the orbital angle, and in which the holder at the other end of the C-arm engages with an X-ray detector, wherein the holder, in the case of a non-isocentric C-arm or in the case of an isocentric C-arm with an ROI that is not located in the isocenter, is displaced in the plane of the arc in parallel in such a manner that the central ray for each position of the orbital movement axis extends through the virtual scan center and the ROI is located entirely within the fan beam.

In the third section adjoining the second section of the focus trajectory, the C-arm remains positioned in the second extreme position of the orbital movement axis, and the holder in the plane of the C-arm is moved parallel in a collision-free manner until a second limiting beam of the fan beam, which is located on the side of the central ray facing the C-arm, is tangential to the ROI.

The focus of the X-ray source can be passed through in any direction on the focus trajectory between a start point and an end point.

DETAILED DESCRIPTION OF THE PREFERRED EMBODIMENT

Preferred embodiments of the invention are explained with reference to the figures.

Figure 1:
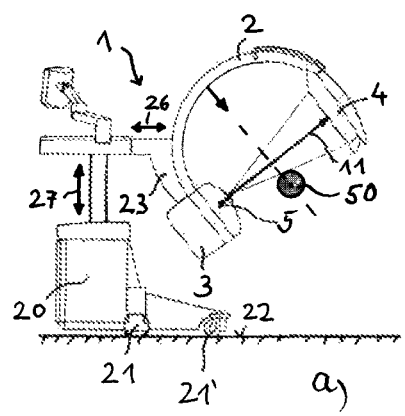
FIG. 1: C-arm X-ray apparatus embodiment with limited rotation range used in connection with methods of preferred embodiments.
Figure 1:
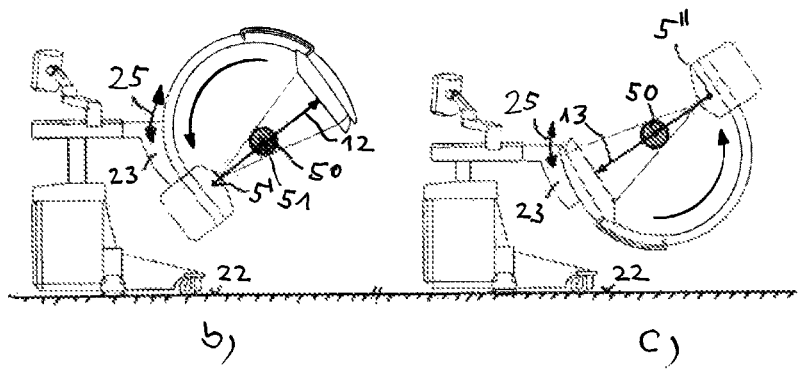
Figure 1:
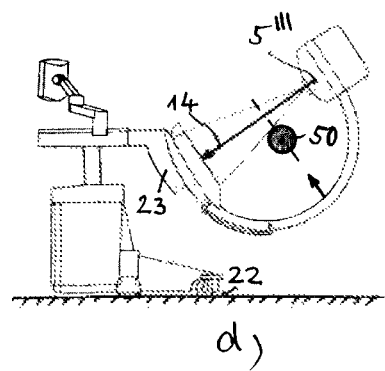

In FIG. 1, a C-arm X-ray apparatus 1 with a limited rotation range is represented in four different phases of the recording process for recording a complete projection data set for a region of interest ("ROI") 50. The example of a C-arm X-ray 1 of FIG. 1 shows an apparatus carriage 20 that can be moved by means of wheels 21, 21' along the floor 22. However, in some embodiments of the invention, it is also provided to mount the C-arm 2 on a stationary floor or ceiling tripod in an adjustable manner.

The C-arm of FIG. 1 is a non-isocentric C-arm, in which the circle center of the C is not on the central ray vector 11, 12, 13, 14. In order to be able to record a rotation scan of an examination object with a ROI, the holder 23 of the C-arm 2 is adjusted during the scan in correlation with the orbital movement in the orbital movement axis 25 in the plane of the C-arm 2, in such a manner that the central ray vector 11, 12, 13, 14 always extends through the virtual scan center 51.

The volume to be reconstructed is in the shape of a cylinder with a height H, wherein the cylinder axis is perpendicular to the plane of the C-arm 2. In the plane of the C-arm 2, the section through the cylindrical volume to be reconstructed represents a circular ROI 50 and the puncture point of the cylinder axis of the plane of the C-arm 2 represents the virtual scan center 51 located in the circle center of the ROI 50. The plane of the C-arm 2 remains fixed in space during the recording of the X-ray projections. In particular, for the space requirement of a C-arm X-ray apparatus 1 during the recording of a scan, it is advantageous if the plane of the C-arm stands vertically in the room. In addition, within the context of certain embodiments of the invention, it is also provided to carry out the scan with another position of the space-fixed plane of the C-arm 2. This is of interest particularly if an intersection plane of the examination object that is in a nonvertical position in the room is to be reconstructed in an artifact-free manner and the examination object can be aligned in such a manner that the desired intersection plane with the ROI 50 contained therein stands vertically in the room.

In FIGS. 1b and 1c, the final positions of a rotation scan with a non-isocentric C-arm 2 are represented. The trajectories of the focus 5', 5" and of the tip of the central ray vector 12, 13, which represents the center of the ray inlet window of the X-ray detector 4, are located on two circular arcs of two space-fixed concentric circles with the stationary virtual scan center as center.

The mobile C-arm X-ray apparatus 1 represented in FIG. 1 has an apparatus carriage 20, which carries a multiply adjustable C-arm 2, which carries, at one end, an X-ray source 3 with a focus 5 and opposite that, arranged at the other end of the C-arm 2, an X-ray detector 4. Between the focus 5 and the center of the X-ray detector 4, a central ray vector 11 is represented, which is located in the plane defined by the C-arm 2. The C-arm 2 is movably mounted in a holder 23 along its periphery. In FIG. 1b, this so-called orbital movement axis 25 is marked by a double arrow. The holder 23 is movable relative to the floor 22 or relative to the apparatus carriage 20 in the plane defined by the C-arm 2. In the example of FIG. 1a, the holder 23 is movable with a horizontal movement axis 26 and with a vertical movement axis 27. In a predetermined angular position of the central ray vector 11 with respect to the floor 22, the C-arm can be moved parallel in the movement area of the horizontal movement axis 26 and of the vertical movement axis 27 in the plane of the C-arm 2 while maintaining its direction.

The C-arm X-ray apparatus 1 is used to make available, for an ROI having a virtual scan center 51, a projection data set that is complete with a view to a Feldkamp 3D reconstruction of a disk-shaped ROI. The C-arm 2 represented as an example in FIG. 1 is a so-called non-isocentric C-arm in which the central ray vector 10, 11, 12, 13 does not extend through the center, not shown, of the C-arm. In the case of a movement of the C-arm 2 in the holder 23 along the periphery of the C-arm 2, the central ray vectors 10, 11, 12, 13 do not extend through a space-fixed point; instead they are tangential in each case to a circle around a virtual scan center 51. Due to synchronous tracking of the C-arm 2 in the horizontal movement axis 26 and the vertical movement axis 27 during the orbital movement in the orbital movement axis 25, an isocentric C-arm is simulated.

Figure 3:
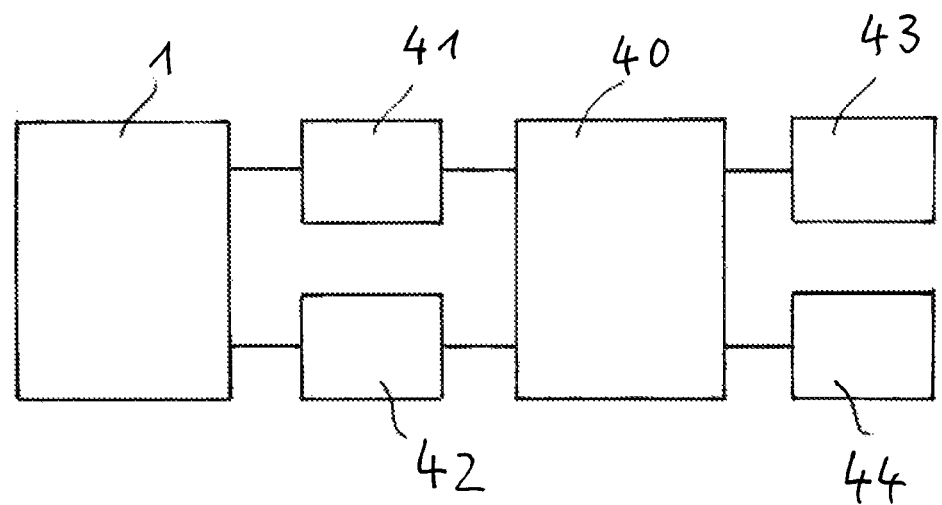
FIG. 3: Control architecture of the C-arm X-ray apparatus of preferred embodiments.

The movement in a horizontal movement axis 26, the vertical movement axis 27 and the orbital movement axis 25 is carried out by a motor, whereas the movements are controlled with the movement control 41 in FIG. 3.

The C-arm 2 in FIG. 1 has a limited rotation range in the orbital movement axis 25 of less than 180°. Using such a limited rotation range, it is not possible to record a complete projection data set for an analytical reconstruction of the disk-shaped cylindrical X-ray volume of the Feldkamp type. In a complete projection data set for the disk-shaped ROI 50 of the central layer having a thickness of one voxel that is located in the plane of the C-arm 2, the missing projection data have to be recorded with additional flat trajectories. For this purpose, the C-arm 2 in FIG. 1a is first positioned, in a first extreme rotation position in which the holder 23 engages at one end of the C-arm 2 with the X-ray source 3, in such a manner that the cone beam extending between the focus 5, 5', 5", 5''' and the X-ray detector 4 does not pass through the ROI 50 just barely, and the first limiting beam of the fan beam 32, which is located on the side of the central ray vector 11, 12, 13, 14 facing away from the C-arm 2, is tangential to the ROI 50.

Starting with this initial position, the C-arm 2, with maintenance of the direction of the central ray vector 11 in the first extreme rotation position of the C-arm 2, is moved by movements in the horizontal movement axis 26 and the vertical movement axis 27 toward the virtual scan center 51, until the central ray 12 in the position of the C-arm 2 in FIG. 1b extends through the virtual scan center 51 in the center of the ROI 50. The entire ROI 50 is contained in the position of the C-arm 2 of FIG. 1b completely in the cone beam of the C-arm X-ray apparatus 1.

Between the position of the C-arm 2 in FIG. 1b and the position of the C-arm 2 in FIG. 1c, the central ray vector 12, 13 rotates in such a manner that it always extends through the virtual scan center 51, and in the process it is moved from the first extreme rotation position in FIG. 1b into the second extreme rotation position in FIG. 1c, in which the holder 23 engages at the other end of the C-arm 2 with the X-ray detector 4. The two extreme rotation positions of FIGS. 1b and 1c characterize the end positions of the movement of the C-arm 2 in the holder 23 along the orbital movement axis 25. The two extreme rotation positions on the orbital movement axis are spaced apart by an angle of at least 180° minus fan angle.

Starting with the position of the C-arm 2 in FIG. 1c, the C-arm 2 is moved by movements in the horizontal movement axis 26 and the vertical movement axis 27 in the case of unchanged direction of the central ray 13 in the second extreme rotation position of the C-arm 2 away from the ROI 50 until the ROI 50 comes to be located entirely just outside of the cone beam, and a second limiting beam of the fan beam 32, which is located on the side of the central ray vector 11, 12, 13, 14 facing the C-arm 2, is tangential to the ROI 50.

The rotation of the central ray vector 12, 13 between the positions of the C-arm 2 in FIGS. 1b and 1c can occur in an isocentric C-arm solely by the orbital movement along the periphery thereof in the holder 23, whereas, in the case of a non-isocentric C-arm as in FIGS. 1b and 1c, a tracking of the horizontal movement axis 26 and of the vertical movement axis 27 during the orbital movement in the orbital movement axis 25 is required. In the case of an isocentric C-arm, it can be advantageous for the virtual scan center to be placed not in the isocenter of the C-arm but, for example, close to the detector between the isocenter and the FPD. In this case, it is necessary, even in the case of an isocentric C-arm, to move the holder of the C-arm in the plane of the C-arm in order to keep the central ray on the virtual scan center.

According to the description of FIGS. 1a to 1c, in the practical use of the method, the C-arm is first moved in a collision-free manner into the position at the beginning of the scan, as represented in FIG. 1a. This positioning movement occurs without radiation and the projection views of the scan are recorded only after the start of the scanning movement. At the time of the completion of the scan, the C-arm 2 is in the position represented in FIG. 1d.

For the method for recording the projection data set, it does not matter in which direction the trajectories of the X-ray source and of the detector are passed through. Therefore, it does not matter whether the C-arm 2 is in the position shown in FIG. 1d at the beginning of the scan. At the time of the completion of a scan passed through in the reverse direction compared to that of the description of FIGS. 1a to 1d, the C-arm 2 is in the position represented in FIG. 1a.

Figure 2:
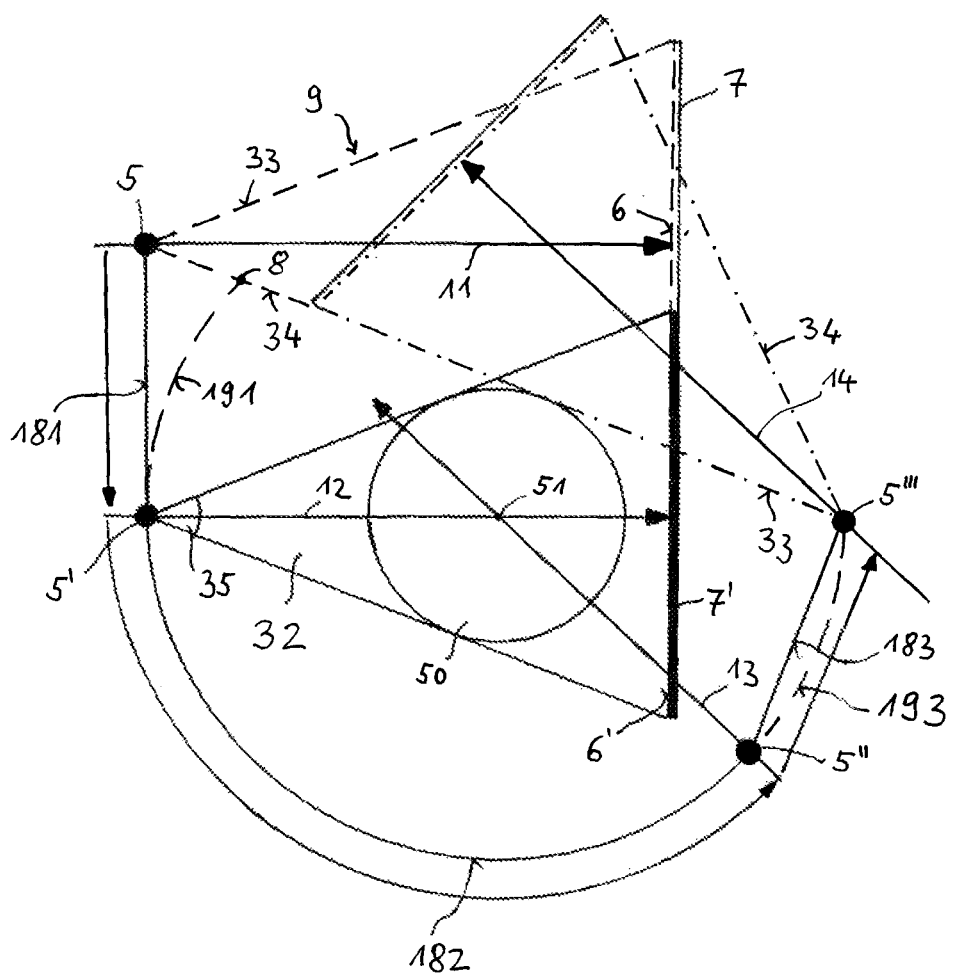
FIG. 2: Focus trajectory and projection geometries for recording a complete projection data set according to preferred embodiments.

FIG. 2 represents two focus trajectories of the focus 5, 5', 5", 5'", shown as examples, and the associated central ray vectors 11, 12, 13, 14 by means of which a complete projection data set for the ROI 50 in the plane of the C-arm 2 can be achieved.

FIG. 2 represents an X-ray image recording system 9 with a focus 5, with an X-ray detector designed as a flat panel detector (FPD) 7 and with a central ray vector 11, which extends from the focus 5 to the center 6 of the ray inlet window 6. The focus 5, 5', 5", 5'" is moved along a focus trajectory, which comprises, or in some embodiments consists of three sections 181, 182, 183, wherein, in the case of the first section 181 of the first focus trajectory, and in the case of the third section 183 of the first focus trajectory, the central ray vector 11, 12, 13, 14 is moved parallel in a stationary coordinate system. The second section 182 of the first focus trajectory is characterized by a rotation of the central ray vector 12, 13 about the virtual scan center 51 in the center of the ROI 50. In FIG. 2, the ROI 50 located in the plane of the C-arm 2 is represented, and of the cone beam extending between the focus 5' and the FPD 7', only the flat fan beam 32 located in this plane with the first and second limiting beams 34, 33 is represented. The first limiting beam 34 of the fan beam 32 is located here on the side of the central ray vector (11, 12, 13, 14) facing away from the C-arm (2), and the second limiting beam 33 of the fan beam 32 is located here on the side of the central ray vector (11, 12, 13, 14) facing the C-arm (2). During the pass through the first focus trajectory, all the fan beams by means of which the projection views are recorded are located in the plane of the C-arm 2, and the entire area of the disk-shaped ROI 50 is contained in the central layer with circular cross-sectional surface completely in the cone beam in each of the one-dimensional projections. The ROI of the example consists of an arrangement of voxels that represent a disk having the height of a voxel.

The focus 5' at the beginning of the second section 182 of the first focus trajectory is considered first. The fan beam 32 with a fan angle 35 passes completely through the ROI 50. The rotation angle in the second section 182 of the first focus trajectory is 180° minus fan angle 35, between the positions of the focus 5' and 5".

If two sections 191 and 193 of a second focus trajectory adjoin the second section 182 of the focus trajectory, wherein the central ray vector would extend through the virtual scan center 51, then one would have the situation of a fan beam scan with a rotation angle range of 180° plus fan angle 35. This represents the known condition for obtaining a complete projection data set for the reconstruction of the ROI 50 in the plane of the C-arm 2, if the focus rotates from the end point 8 of the first section 191 of the second focus trajectory to the position of the focus 5'" around the virtual scan center 51 with a rotation angle range of 180° plus fan angle. If one considers a focus at the end point 8 with a central ray through the virtual scan center 51, then the fan beam is delimited by the second limiting beam 33, wherein the fan beam in the position of the focus 5'" in the case of a central ray through the virtual scan center 51 is delimited by the first limiting beam 34, which coincides with the second limiting beam 33.

In the case of the method according to some embodiments of the invention for recording a complete projection data set for the reconstruction of the ROI 50 in the plane of the C-arm 2, a first section 181 and a third section 183 of the first focus trajectory adjoin the second section 182 of the first focus trajectory, and in the case of the former sections, the central ray vector 11, 12, 13, 14 is moved parallel. The first limiting beam 34 in the position of the focus 5 at the beginning of the first section 181 of the first focus trajectory coincides with the second limiting beam 33 in the position of the focus 5'".

The parallel movement of the central ray vector with a movement of the focus 5 up to a position of the focus 5' in the first section 181 of the first focus trajectory and with a movement of the focus 5" up to a position of the focus 5'" in the third section 183 of the first focus trajectory completes the incomplete projection data set, which is obtained in the second section 182 of the first focus trajectory in the case of a rotation of the central ray vector 12, 13 by an angle of 180° minus fan angle 35 to form a complete projection data set. Each point within the ROI 50 is crossed by projection beams under angles between 0° and 180° relative to a coordinate axis connected to the ROI through the virtual scan center.

In the case of parallel motion of the central ray vector 11, 12, 13, 14 in the first section 181 of the first focus trajectory, the ROI 50 is irradiated with an increasingly larger portion of the fan beam 32, whereas in the case of parallel motion of the central ray 11, 12, 13, 14 in the third section 183 of the first focus trajectory, the ROI 50 is irradiated with an increasingly smaller portion of the fan beam 32. It is provided that those portions of the fan beam 32 that do not collide with the ROI 50 are removed by a movable and automatically controlled primary radiation diaphragm between the X-ray source and the ROI. The primary beam diaphragm, which is preferably controlled by an electric motor, is moved preferably synchronously with the movement of the holder 23.

The paths on which the focus 5, 5', 5", 5'" is moved in the first and in the third section of the focus trajectory can be selected largely arbitrarily, as long as the ROI 50 or a patient bench, not represented, does not collide with the X-ray source 3, with the X-ray radiation receiver 4 or with the C-arm 2 in FIG. 1. In particular, it does not matter in which direction the movement through the focus trajectory occurs. The movement through the focus trajectory in the one or in the other direction yields identical projection data sets.

As can be seen in FIG. 2, in the first section 181 of the first focus trajectory, during the movement of the focus 5 in the direction toward the position of the focus 5', the distance between the focus 5, 5' and the virtual scan center 51 is greater than the distance of the focus 5', 5" in the area of the second section 182 of the first focus trajectory with the rotation movement and that, in the third section 183 of the first focus trajectory, in the case of movement of the focus 5" in the direction toward the position of the focus 5''', the distance between the focus 5", 5''' and the virtual scan center 51 is smaller than the distance of the focus 5', 5" in the area between the second section 182 of the first focus trajectory with the rotation movement of the central ray vector. It is possible, for example, for the first and third sections 191, 193 of the second focus trajectory to adjoin the second section 182 of the first focus trajectory, wherein the focus 5, 5', 5", 5''' moves on a circular path with a rotation angle of 180° plus fan angle, and the central ray vector 11, 12, 13, 14 would be moved parallel with unchanged direction in the first and third sections 191, 193 of the second focus trajectory.

In FIG. 3, the control architecture for a C-arm X-ray apparatus 1 is represented, which is suitable for carrying out the method according to the invention for recording a complete projection data set. A movement controller 41 controls all the motor-driven movements of the C-arm X-ray apparatus 1. In the example of FIGS. 1*a* to 1*d*, the horizontal movement axis 26, the vertical movement axis 27, and the orbital movement axis 25 are provided as motor-driven axes. By means of the horizontal movement axis 26, the vertical movement axis 27, and the orbital movement axis 25, it is possible, in the case of a plane of the C-arm 2 that stands vertically in the room, to simulate, in the movement phase of the rotation scan, an isocentric C-arm and to move the holder 23 of the C-arm 2 parallel in this plane. By means of the movement control 41, it is provided to control the movement of the primary beam diaphragm, which is preferably controlled by an electric motor, synchronously with the movement of the holder 23, in such a manner that, in the first section 181, 191, 195 of the focus trajectory and in the third section 183, 193, 197 of the focus trajectory, the portion of the fan beam 32 that is located outside of the ROI 50 is removed.

In the context of embodiments of the invention, it is provided to carry out the method for recording a projection data set with flat focus and detected trajectories with a C-arm X-ray apparatus 1 in such a manner that the C-arm plane thereof is pivoted in the room against the vertical. For this purpose, an additional motor-driven movement axis is provided, which allows a motor-controlled movement transversely to the horizontal movement axis 26 and to the vertical movement axis 27. This additional movement axis can be a transverse movement axis in which the holder 23 of the C-arm 2 can be moved perpendicularly to the plane defined by the directions of the horizontal movement axis 26 and the vertical movement axis 27.

It is provided to integrate a collision protection function in the movement controller. Here, it is possible to provide that, in the case of an imminent risk of collision between portions of the C-arm X-ray apparatus 1 with parts of the patient bench, alternative focus trajectories for the X-ray focus that deviate from the planned focus trajectory are passed through autonomously by the movement controller 41. All the processes that are connected with the X-ray image generation and the X-ray image recording during the scan are controlled by an image recording control 42. The synchronization of the two controls 41, 42 occurs by the central computation unit 40, which has an input means 43 and an output means 44. It is provided to integrate means in the computation unit for image processing and for 3D reconstruction based on the recorded projection data.

Figure 4:
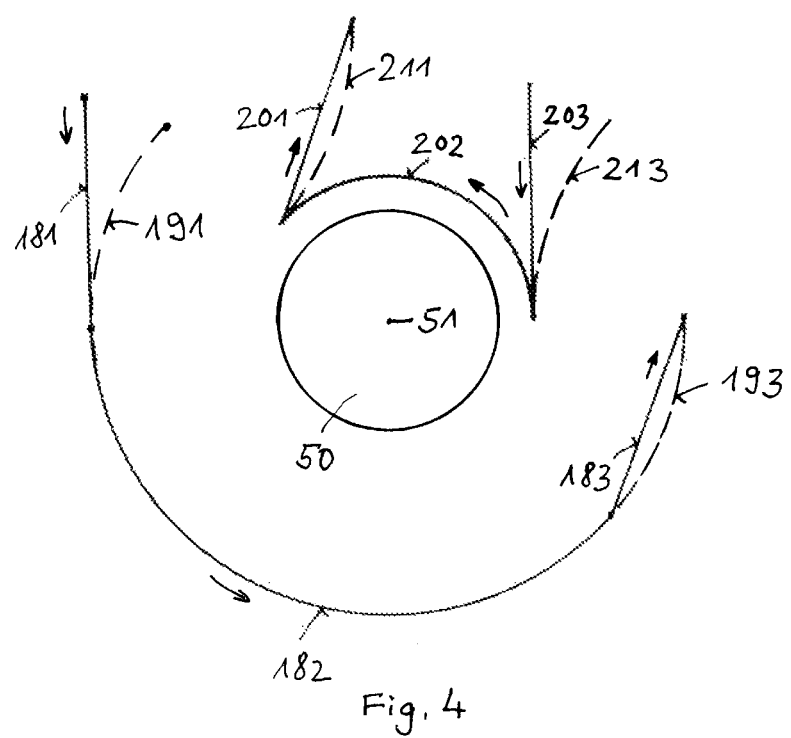
FIG. 4: Second focus trajectory and second detector trajectory according to the method of preferred embodiments of the invention for recording a complete projection data set.

In FIG. 4, focus trajectories and detector trajectories of the center of the ray inlet window of the X-ray detector for the method according to the invention for recording a complete projection data set are represented.

The first focus trajectory of the focus 5 comprising, or in some embodiments consisting of, the sections 181, 182, 183 is passed through in the direction of the arrow. The associated first detector trajectory comprises the sections 203, 202, 201, which are passed through consecutively. If the focus 5 is moved along a focus trajectory that consists of the first section 191 of the second focus trajectory, the second section 182 of the first focus trajectory, and the third section 193 of the second focus trajectory, then the center of the ray inlet window 6 and consequently the tip of the central ray vector 11, 12, 13, 14 move first on the first section 213 of the second detector trajectory, than on the second section 202 of the first detector trajectory, and finally on the third section 211 of the second detector trajectory.

Figure 5:
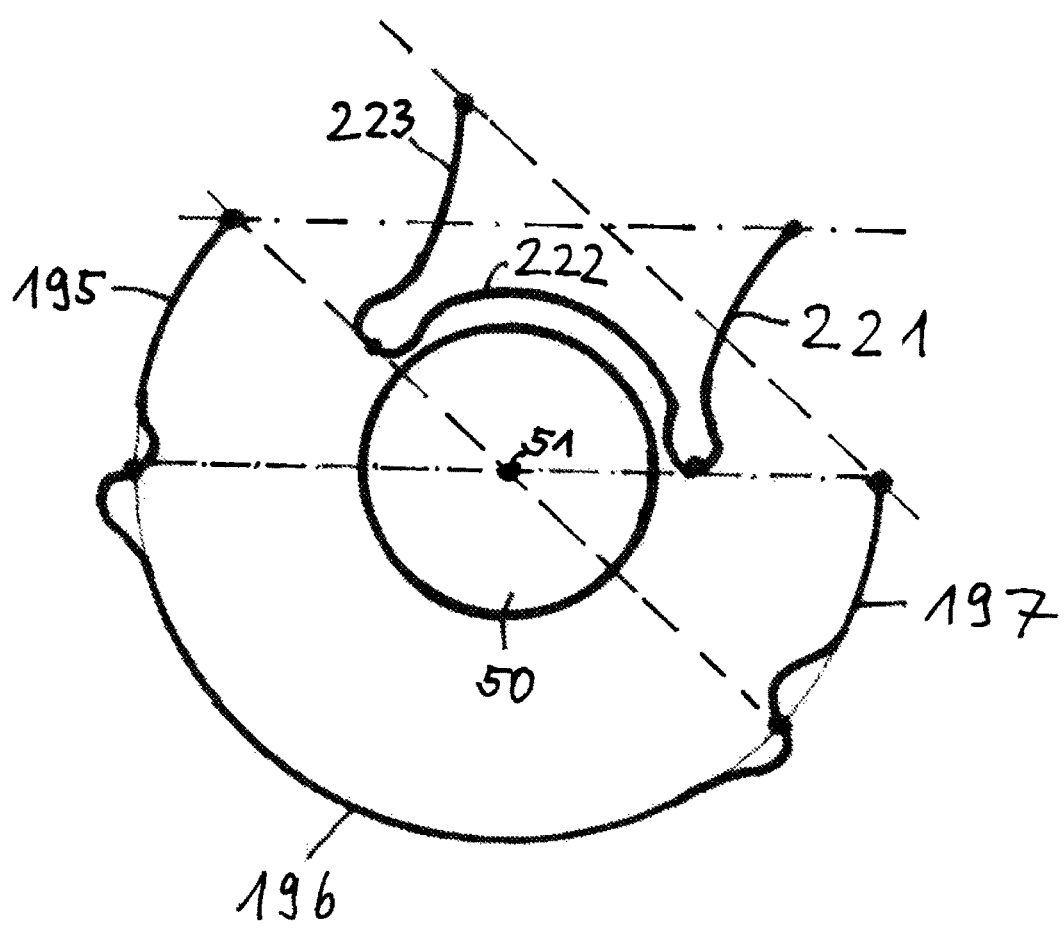
FIG. 5: Third focus trajectory and third detector trajectory according to the method of preferred embodiments of the invention for a limited detector acceleration.

In FIG. 5, the trajectories of the focus and of the center of the ray inlet window of the X-ray detector according to the method of the invention are represented, wherein, in comparison to the trajectories of FIG. 4, the acceleration of the X-ray detector is limited at constant speed of the X-ray source. The second detector trajectory of FIG. 4 has abrupt changes in the direction of the path at the junction between the sections 203 and 202 and at the junction between the sections 202 and 201, which leads to triggering of undesired high accelerations and oscillations of the C-arm. In FIG. 5, as an example, a third focus trajectory with the sections 195, 196, 197 and a third detector trajectory with the sections 221, 222, 223 are represented. The end points of the sections of the respective trajectories are marked by points. In the first movement phase of the C-arm, which is characterized by the first section 195 of the third focus trajectory and by the first section 221 of the third detector trajectory, the central ray vector is moved in the area between the dot-and-dash lines perpendicularly and parallel to its direction. In the second movement phase of the C-arm, which is characterized by the second section 196 of the third focus trajectory and the second section 222 of the third detector trajectory, the central ray vector rotates around the virtual scan center 51, wherein, at the beginning and at the end of the second movement phase, the central ray is shifted in addition parallel along its direction. In the third movement phase of the C-arm, which is characterized by the third section 197 of the third focus trajectory and the third section 223 of the third detector trajectory, the central ray vector is moved in the area between the broken lines perpendicularly and parallel to its direction. In contrast to the detector trajectories of FIG. 4, the third detector trajectory with the sections 221, 222, 223 no longer has any abrupt changes in direction. On the other hand, the third focus trajectory with the sections 195, 196, 197 has deviations from the circular arc-shaped focus trajectory of FIG. 4. The junctions between the first and the second sections 195 and 196 and between the second and the third sections 196 and 197 of the third focus trajectory are designed in the example such that no abrupt changes in direction in the focus trajectory defined in sections with the sections (195, 196, 197) and in the detected trajectory defined in sections with the sections (221, 222, 223) occur. For this purpose, the focus trajectory at the junction between the first section (195) and the second section (196) as well as at the junction between the second section (196) and the third section (197) must extend in the radial direction relative to the virtual scan center (51).

It is desirable to prevent an abrupt change in direction, as encountered, for example, at the junction between the second section 182 and the third section 183 of the first focus trajectory. An abrupt change in direction in the focus trajectory or in the detector trajectory, owing to the large weights of the ends of the C-arm 2 and due to the associated abrupt change in the velocity vector, leads to an impulse applied to the C-arm, which can lead to undesired oscillations of the C-arm, in particular since the impulse occurs in the position of the C-arm represented in FIG. 1c, in which position the tilting torques of the C-arm 2 applied to the holder 23 and the horizontal movement axis 26 and the vertical movement axis 27 of the C-arm 2 are at a maximum from all the positions of the C-arm 2. If one considers the weights of the X-ray generator and of the FPD, then the X-ray generator has a considerably greater weight compared to the FPD. In order to in the case of C-arm X-ray apparatuses 1, which in addition to the electrically control led movement also allows a manual movement, a compensatory weight is provided to compensate for torques in the area of the FPD, which also makes the FPD sensitive to changes in the velocity vector. The torsional stiffness of the C-arm 2 is similarly low in the positions of FIGS. 1a and 1b as well as in the positions 1c and 1d.

In the individual movement phases, parallel shifts of the central ray vector are provided along its direction, preferably for avoiding obstacles and preventing collisions. Thus, the focus trajectory of FIG. 5 in the interior of the sections (195, 196, 197) can have deviations from the circle arc with the circle center in the virtual scan center, as long as the ROI 50 in the second section (196) is reproduced completely on the X-ray detector 4 and as long as in all the sections (195, 196, 197) of the focus trajectory, the X-ray image recording system 9 is moved in a collision-free manner around the examination object with the ROI 50. It is provided to allow the focus trajectory (195, 196, 197) to oscillate in a circle arc with the center in the virtual scan center 51. In particular, it can be desirable to increase the distance between the second section (222) of the detector trajectory and the ROI 50 in the region of the junctions between the first section (221) and the second section (222) of the detector trajectory as well as at the junction between the second section (222) and the third section (223) of the detector trajectory.

The method according to the invention for recording a scan of a region of interest ROI (50) having a virtual scan center (51) located in the center of the ROI (50) comprises a scan consisting of a series of X-ray projection views that provide a complete set of X-ray projection data of the ROI (50) in the central layer in the plane of the C-arm (2) for a 3D reconstruction. Here, the series of X-ray projection views is recorded using a C-arm X-ray apparatus (1), which has a C-arm (2) with a space-fixed plane, in which the C-arm (2) can be moved parallel with a holder (23) that can be multiply adjusted by means of a motor, and it is mounted so it can be moved by means of a motor in the holder (23) along its periphery in an orbital movement axis (25) between a first and a second extreme position, and wherein the C-arm (2) comprises an X-ray image recording system (9) with an X-ray source (3) arranged at an end of the C-arm (2) and with an X-ray detector (4) arranged in an opposite position at the other end of the C-arm (2), wherein, in the first extreme position, the holder (23) engages at one end of the C-arm (2) with the X-ray source (3), and, wherein, in the second extreme position, the holder (23) engages at the other end of the C-arm (2) with the X-ray detector (4), and wherein the X-ray image recording system (9) is characterized by a central ray vector (11, 12, 13, 14), which extends from the focus (5, 5', 5", 5''') of the X-ray source (3) to the center of the radiation inlet window (6) of the X-ray detector (4), and which stands vertically on the radiation inlet window (6) of the X-ray detector (4), and generates a cone beam which contains, in the plane of the C-arm (2), a fan beam (32) with a fan angle (35), wherein the focus (5, 5', 5", 5''') of the X-ray source (3) is moved, with recording of the series of X-ray projection views, along a flat coherent focus trajectory between a start point and an end point in any desired direction.

At the start point of the focus trajectory, the C-arm (2) in the orbital movement axis (25) is positioned in the first extreme position, and the adjustable holder (23) of the C-arm (2) is positioned in such a manner that a first limiting beam (34) of the fan beam (32), which is located on the side of the central ray vector (11, 12, 13, 14) facing away from the C-arm (2), is tangential to the ROI (50), [sic]

In a first section (181, 191, 195) of the focus trajectory, the holder (23) is moved parallel in the plane of the C-arm (2), until the central ray vector (11, 12, 13, 14) extends through the virtual scan center (51) and the ROI (50) is located entirely within the fan beam (32), [sic]

In a second section (182, 196) of the focus trajectory, the C-arm (2) is moved in the orbital movement axis (25) from the first extreme position into a second extreme position, in which the holder (23) engages at the other end of the C-arm (2) with the X-ray detector (4), wherein the angle range of the orbital movement between the first and the second extreme position is at least 180° minus fan angle (35), and the holder (23) in the plane of the C-arm (2) is moved parallel in such a manner that the central ray vector (11, 12, 13, 14) extends through the virtual scan center (51) and the ROI (50) is located entirely within the fan beam (32), [sic]

In a third section (183, 193, 197) of the trajectory, the C-arm (2) remains positioned in the orbital movement axis (25) in the second extreme position, and the holder (23) is moved parallel in the plane of the C-arm (2), until a second limiting beam (33) of the fan beam (32), which is located on the side of the central ray vector (11, 12, 13, 14) facing the C-arm (2), is tangential to the ROI (50).

It is provided to select the sections (181, 182, 183, 191, 193, 195, 196, 197) of the focus trajectory in such a manner that the focus trajectory composed in sections and a detector trajectory characterizing the movement of the center of the ray inlet window (6) of the X-ray detector (4) and composed in sections from the sections (201, 202, 203, 211, 213, 221, 222, 223) have no abrupt changes in direction.

It is provided that focus trajectory comprising the sections (195, 196, 197) oscillate around a circle arc with a circle center in the virtual scan center (51), and that the focus trajectory in the junction between the first section (195) and the second section (196) as well as on the junction between the second section (196) and the third section (197) is selected in such a manner that it extends in the radial direction with respect to the virtual scan center (51).

What is claimed is:

1. A method for recording a scan of a region of interest (ROI) using a C-arm X-ray apparatus with a virtual scan center located in the center of the ROI, wherein the scan comprises a series of X-ray projection views providing a complete set of X-ray projection data of the ROI in the plane of the C-arm X-ray apparatus for a 3D reconstruction, and wherein the series of X-ray projection views is recorded using the C-arm X-ray apparatus, the X-ray apparatus comprising a C-arm with a space-fixed plane, the C-arm being mounted in such a manner that it can be moved parallel with a holder which is multiply adjustable by means of a motor, the C-arm further being mounted in such a manner that it can be moved by means of a motor in the holder along its periphery in an orbital movement axis, between a first and a second extreme position, the method comprising:

at the start point of the focus trajectory:
  positioning the C-arm in the orbital movement axis in the first extreme position; and
  positioning the adjustable holder of the C-arm in such a manner that a first limiting beam of the fan beam, which is located on the side of the central ray vector facing away from the C-arm, is tangential to the ROI;
in a first section of the focus trajectory, moving the holder parallel in the plane of the C-arm until the central ray vector extends through the virtual scan center and the ROI is located completely within the fan beam;
in a second section of the focus trajectory:
  moving the C-arm in the orbital movement axis from the first extreme position into a second extreme position, in which the holder engages at the other end of the C-arm with the X-ray detector, and wherein the angle area of the orbital movement between the first and the second extreme position is at least 180° minus fan angle, and
  moving the holder parallel in the plane of the C-arm in such a manner that the central ray vector extends through the virtual scan center, and the ROI is located entirely within the fan beam; and
in a third section of the focus trajectory:
  maintaining the C-arm in the orbital movement axis in the second extreme position, and
  moving the holder parallel in the plane of the C-arm until a second limiting beam of the fan beam, which is located on the side of the central ray vector facing the C-arm, is tangential to the ROI;
wherein the movements of the holder and of the C-arm in the orbital movement axis are controlled by a movement control;
wherein the C-arm comprises an X-ray image recording system, the X-ray image recording system comprising:
  an X-ray source disposed at a first end of the C-arm and comprising a primary radiation diaphragm controlled by means of a motor; and
  an X-ray detector disposed at a second end of the C-arm opposite the first end;
wherein, at the second extreme position, the holder engages at the first end of the C-arm with the X-ray source;
wherein the X-ray image recording system is characterized by a central ray vector extending from a focus of the X-ray source to a center of a ray inlet window of the X-ray detector, the central ray vector standing vertically on the ray inlet window;
wherein the X-ray image recording system generates a cone beam which contains, in the plane of the C-arm, a fan beam having a fan angle; and
wherein the focus of the X-ray source is moved, while the X-ray projection views are recorded, along a flat coherent focus trajectory between a start point and an end point in any direction.

2. The method for recording a scan according to claim 1, wherein the first, second, and third sections of the focus trajectory are selected such that a detector trajectory characterizing the movement of the center of the radiation inlet window of the X-ray detector has no abrupt changes in direction.

3. The method for recording a scan according to claim 2, wherein the focus trajectory comprises the first, second, and third sections oscillating around a circular arc about the virtual scan center, and wherein the focus trajectory at the junction between the first section and the second section and the focus trajectory at the junction between the second section and the third section extend in a radial direction relative to the virtual scan center.

4. The method for recording a scan according to claim 1, wherein, in the first and third sections of the focus trajectory, a portion of the fan beam that is located outside of the ROI is removed by means of the primary radiation diaphragm, wherein the primary radiation diaphragm is moved by means of a motor by the movement control synchronously with the movement of the holder.

5. The method for recording a scan according to claim 2, wherein, in the first and third sections of the focus trajectory, a portion of the fan beam that is located outside of the ROI is removed by means of the primary radiation diaphragm, wherein the primary radiation diaphragm is moved by means of a motor by the movement control synchronously with the movement of the holder.

6. The method for recording a scan according to claim 3, wherein, in the first and third sections of the focus trajectory, a portion of the fan beam that is located outside of the ROI is removed by means of the primary radiation diaphragm, wherein the primary radiation diaphragm is moved by means of a motor by the movement control synchronously with the movement of the holder.

* * * * *